(12) United States Patent
Hoaki et al.

(10) Patent No.: US 6,265,162 B1
(45) Date of Patent: Jul. 24, 2001

(54) METHOD OF IDENTIFYING, DETECTING AND MONITORING MICROORGANISMS BY AN AROMATIC RING HYDROXYLASE DIOXYGENASE GENE

(75) Inventors: Toshihiro Hoaki; Asaka Suzuki, both of Chiba (JP)

(73) Assignee: Taisei Corporation, Tokyo (JP)

( * ) Notice: Subject to any disclaimer, the term of this patent is extended or adjusted under 35 U.S.C. 154(b) by 0 days.

(21) Appl. No.: 09/073,377

(22) Filed: May 5, 1998

(51) Int. Cl.[7] ........................................ C12Q 1/68

(52) U.S. Cl. ........................................... 435/6

(58) Field of Search .................. 435/6; 536/24.32; 530/300

(56) References Cited

U.S. PATENT DOCUMENTS 5,573,910 * 11/1996 Deretic et al. ........................... 435/6

OTHER PUBLICATIONS

Chemical Patent Index, Documentation Abstracts and Journal, Derwent Publications, London 1997, No. 97–497312/46 on JP 09234970 A.

* cited by examiner

Primary Examiner—Scott W. Houtteman
(74) Attorney, Agent, or Firm—Fish & Richardson, P.C.

(57) ABSTRACT

The present invention relates to a method of detecting microorganisms by use of preserved amino acid sequences on a 1,2-dioxygenase gene; a method of identifying microorganisms by use of a nucleotide sequence coding for an amino acid sequence intervened between preserved amino acid sequences on a 1,2-dioxygenase gene; and a method of monitoring biological degradation of crude oil wherein the multiplication of aromatic-degrading bacteria degrading aromatic compounds contained in crude oil is detected using nucleotide sequences coding for preserved amino acid on a 1,2-dioxygenase gene. According to the present invention, microorganisms having a 1,2-dioxygenase gene can be detected easily and rapidly. In addition, aromatic-degrading bacteria can be identified easily, rapidly and accurately without using any conventional biological examinations.

11 Claims, 2 Drawing Sheets

Sense primer
  N-terminal
                                            C-terminal
    Cys- Ser- Tyr- His- Gly- Trp
              Phe-

| TGT | AGT | TAT | CAT | GGT | TGG |
|-----|-----|-----|-----|-----|-----|
| TGC | AGC | TAC | CAC | GGC |     |
|     | TCT | TTT |     | GGA |     |
|     | TCC | TTC |     | GGG |     |
|     | TCA |     |     |     |     |
|     | TCG |     |     |     |     |

Primer portion

FIG. 1

Antisense primer
  N-terminal
                                                C-terminal
    Asn- Trp- Lys- Phe- Ala- Ala- Glu-

| AAT | TGG | AAA | TTT | GCT | GCT | GA | A |
| AAC |     | AAG | TTC | GCC | GCC | GA | G |
|     |     |     |     | GCA | GCA |    |   |
|     |     |     |     | GCG | GCG |    |   |

Primer portion                    Deleted and
                                   not used

FIG. 2

PCR primer

Sense primer; 18-mer

5'-TG(T/C) AG(T/C) T(A/T)(T/C) CA(T/C) GG(G/A/T/C) TGG- 3'

Antisense primer; 20-mer

5'-TC(G/A/T/C)GC (G/A/T/C)GC (A/G)AA (T/C)TT CCA (A/G)TT -3'

( ) ; Mix

FIG. 3

METHOD OF IDENTIFYING, DETECTING AND MONITORING MICROORGANISMS BY AN AROMATIC RING HYDROXYLASE DIOXYGENASE GENE

FIELD OF THE INVENTION

The present invention relates to a method of detecting microorganisms at the gene level responsible for an important role in various fields such as medicine, food, chemistry etc. and in environmental protection such as biological degradation of pollutants, water treatment etc., a method of identifying these microorganisms, and a method of monitoring the activity and multiplication of these microorganisms. Specifically, the present invention relates to a method of detecting and identifying aromatic compounds-degrading bacteria as well as a method of monitoring their multiplication.

BACKGROUND OF THE INVENTION

To deal effectively with cases where environmental pollution results from various pollutants, it is necessary to know how pollutants have been degraded or how the degradation has proceeded. In cases where the environment has been polluted with biodegradable pollutant sources such as crude oil, a method of analyzing the concentration of various hydrocarbons in crude oil has conventionally been used to grasp the progress of the biological degradation of crude oil etc. as pollutant sources.

However, the method of analyzing various hydrocarbons in crude oil was problematic in that accurate analysis results are hardly obtained in spite of cumbersome and time-consuming procedures.

Further, such analysis of hydrocarbons in crude oil requires complex instruments, so there are few cases where analytical instruments are installed at a site of environmental sanitation. Accordingly, analytical samples after collection should be stored and transported in many cases to a site where they can be analyzed. However, because these samples are deteriorated during storage and transportation, there are also cases where the obtained results are not reproducible or fail to reflect the state of biological degradation of crude oil at the polluted site.

Hydrocarbons contained in crude oil etc. are divided roughly into saturated hydrocarbons, aromatic hydrocarbons, resin, and asphaltene. Among these components, any of the aromatic hydrocarbons, resin, and asphaltene contain aromatic compounds and thus hardly undergo degradation by microorganisms. Accordingly, the concentration of these aromatic components in crude oil can be used as an indication of the progress of degradation of pollutants such as crude oil etc. However, it is difficult to grasp which components in pollutants such as crude oil etc. have been degraded and which components are not degraded and remain.

Because analysis of aromatic hydrocarbon compounds in crude oil is difficult as described above, it was proposed to use methods of identifying microorganisms degrading hydrocarbons in crude oil in order to know the state of biological degradation in crude oil. In the conventional methods of identifying microorganisms by biological examination based on e.g. assimilability of saccharides, however, there is the problem that accurate results cannot necessarily be obtained in spite of many examination items and cumbersome and time-consuming procedures.

For highly accurate detection of microorganisms having specific functions, a method of utilizing the recent analysis at the gene level using a nucleotide sequence in 16S rRNA from a microbial species is also conceivable. However, because 16S rRNA is a gene possessed by every microorganism, it is difficult to detect only a group of microorganisms having specific metabolic mechanism. For detection using such a gene as 16S rRNA common to microorganisms, it is necessary to conduct the complicated procedures in which a specific nucleotide sequence in 16S rRNA is amplified by PCR and each of the amplified fragments is then cloned and sequenced. In addition, there is less difference in the nucleotide sequence of 16S rRNA among microorganisms of the same genus or species, so it is necessary to determine its long nucleotide sequence by use of a plurality of primers.

SUMMARY OF THE INVENTION

To solve these problems, it is necessary to establish a method of accurately and easily detecting and identifying a microorganism or a group of microorganisms having specific functions. As a result of their eager study to solve these problems, the present inventors found that preserved amino acid sequences are present in the amino acid sequence of aromatic ring hydroxylase dioxygenase (hereinafter abbreviated to dioxygenase) as an ubiquitous enzyme in certain microorganisms, specifically aromatic-degrading bacteria. On the basis of this finding, the present invention was completed using these sequences.

That is, the present first invention is a method of detecting microorganisms by use of nucleotide sequences coding for preserved amino acid sequences on a dioxygenase gene. Here, one of the preserved amino acid sequences is an amino acid sequence consisting of Cys-Ser-Tyr-His-Gly-Trp (SEQ ID NO.:1) or Cys-Ser-Phe-His-Gly-Trp (SEQ ID NO.:2), and the other is the amino acid sequence shown in Glu-Ala-Ala-Phe-Lys-Trp-Asn (SEQ ID NO.:3).

The present second invention is a method of identifying microorganisms by use of a nucleotide sequence coding for an amino acid sequence intervened between preserved amino acid sequences on a dioxygenase gene. Here, one of the preserved amino acid sequences is an amino acid sequence consisting of Cys-Ser-Tyr-His-Gly-Trp (SEQ ID NO.:1) or Cys-Ser-Phe-His-Gly-Trp (SEQ ID NO.:2), and the other is the amino acid sequence shown in Glu-Ala-Ala-Phe-Lys-Trp-Asn (SEQ ID NO.:3). The above microorganisms include aromatic-degrading bacteria.

The present third invention is a method of monitoring biological degradation of crude oil wherein the multiplication of aromatic compounds in crude oil degrading bacteria is detected using nucleotide sequences coding for preserved amino acid sequences preserved on a dioxygenase gene. Here, one of the preserved amino acid sequences is an amino acid sequence consisting of Cys-Ser-Tyr-His-Gly-Trp (SEQ ID NO.:1) or Cys-Ser-Phe-His-Gly-Trp (SEQ ID NO.:2), and the other is the amino acid sequence shown in Glu-Ala-Ala-Phe-Lys-Trp-Asn (SEQ ID NO.:3).

BRIEF DESCRIPTION OF THE DRAWINGS

FIG. 1 shows preserved amino acid sequences in 1,2-dioxygenase.

FIG. 2 shows another preserved amino acid sequence in 1,2-dioxygenase.

FIG. 3 shows a sense primer and antisense primer used in PCR.

DETAILED DESCRIPTION OF THE INVENTION

Hereinafter, the present invention is described in detail.

The present invention relates to a method of detecting microorganisms by use of nucleotide sequences coding for specific amino acid sequences located on a gene of aromatic ring hydroxylase dioxygenase as an ubiquitous enzyme in certain microorganisms and also to a method of identifying detected microorganisms by said nucleotide sequences. Further, the present invention relates to a method of monitoring biological degradation of crude oil by detection, with said nucleotide sequences, of whether microorganisms having said enzyme are multiplied in crude oil.

Specifically, the present invention relates to a method of detecting said microorganism by determining whether or not a PCR product can be obtained in PCR where the nucleotide sequences coding for preserved amino acid sequences on said dioxygenase gene are used as primers and the DNA of the microorganism to be detected is used as a template.

Aromatic ring hydroxylase dioxygenase, also called two-oxygen-atom-adding enzyme, is an enzyme involved in forming a diol compound by adding oxygen atoms to an aromatic ring. Aromatic ring hydroxylase dioxygenase is an intramolecular dioxygenase requiring iron, heme, copper etc. as co-factors, where one substrate receives 2 oxygen atoms in almost all cases.

Aromatic ring hydroxylase dioxygenase is distributed widely in aromatic compounds-degrading bacteria, and its gene is present on the chromosome in some cases or on a plasmid in other cases. This enzyme is a multi-component enzyme with a molecular weight of about 128,000 composed of 4 subunits, that is, one large subunit (molecular weight: about 51,000), one small subunit (molecular weight: about 22,000), ferredoxin (molecular weight: about 12,000) and ferredoxin reductatse (molecular weight: about 43,000).

When amino acid sequences coded for by aromatic ring hydroxylase dioxygenase genes from a plurality of microorganisms were determined, it was revealed that ubiquitous preserved amino acid sequences are present in the large subunit of this enzyme. These sequences are shown in the amino acid sequences Cys-Ser-Tyr-His-Gly-Trp (SEQ ID NO. :1) or Cys-Ser-Phe-His-Gly-Trp (SEQ ID NO.:2) and Glu-Ala-Ala-Phe-Lys-Trp-Asn (SEQ ID NO.:3). Among these sequences, highly preserved regions are underlined.

Accordingly, nucleotide sequences coding for these amino acid sequences can be used as primers in PCR for amplifying an amino acid sequence intervened between these amino acid sequences. In the amino acid sequence of the large subunit of aromatic ring hydroxylase dioxygenase, Cys-Ser-Tyr-His-Gly-Trp (SEQ ID NO.:1) (referred to hereinafter as amino acid sequence 1) or Cys-Ser-Phe-His-Gly-Trp (SEQ ID NO.:2) (referred to hereinafter as amino acid sequence 2) is located upstream from Glu-Ala-Ala-Phe-Lys-Trp-Asn (SEQ ID NO.:3) (referred to hereinafter as amino acid sequence 3), and thus a nucleotide sequence coding for the amino acid sequence 1 or 2 is used as a sense primer, and a nucleotide sequence coding for the amino acid sequence 3 is used as an antisense primer.

The nucleotide sequences coding for the amino acid sequences 1 to 3 may be used as primers for PCR, or primers may be designed on the basis of these sequences. By use of these primers, a nucleotide sequence coding for an amino acid sequence therebetween is amplified as a DNA fragment. Thereafter, the amplified DNA fragment or hybridized DNA fragment is detected by electrophoresis, DNA hybridization etc. to detect specific microorganisms.

Amino acid sequences 1 to 3 are used as sense and antisense primers as described above so that for a plurality of microorganisms, a nucleotide sequence coding for an amino acid sequence therebetween is amplified as a DNA fragment and then determined by a conventional method such as dideoxy method or the like.

Such nucleotide sequences are different among microorganisms of the same species or even the same strain and often have significant differences even in comparison among microorganisms of the same species, as opposed to nucleotide sequences from the above-described 16S rRNA which show less difference among microorganisms of the same genus, species and strain. Accordingly, such DNA fragments can be used as signature nucleotide sequences to identify the microorganisms.

Further, because the nucleotide sequence amplified by PCR has the specificity as described above, the nucleotide sequence obtained in the manner as described above can be used as a probe as such. Further, a very specific probe used for identification at species or strain levels can be obtained by subjecting to a multiple test a nucleotide sequence obtained in the same manner as above from a related bacterial species.

These probes can be used for specific detection and identification of target microorganisms from a natural microbial habitat containing a large number of unknown microorganisms. Further, these probes can also be used to select unidentified new species.

The microorganisms capable of detection and identification by the detection/identification method of the invention are not particularly limited as far as they are microorganisms having dioxygenase. However, aromatic-degrading bacteria degrading aromatic compounds are preferably used. The aromatic-degrading bacteria refer to bacteria requiring and degrading aromatic compounds such as biphenyl, toluene, naphthalene etc. as substrates.

Specifically, mention can be made of aromatic-degrading bacteria classified into the genera Pseudomonas, Alcaligenes, Rhodococcus, Acinetobacter, and Sphingomonas. The present invention can be used preferably to detect and identify such aromatic-degrading bacteria.

Although biphenyl, toluene, naphthalene etc. are aromatic compounds contained in crude oil, accurate and rapid measurement of the amount of these compounds in crude oil is difficult as described above in cases where pollution with crude oil has occurred. Accordingly, multiplication of aromatic-degrading bacteria by degrading these compounds in crude oil can be examined using the detection/identification method of the invention to monitor how the biological degradation of crude oil has proceeded.

As stated above, the microorganisms having the dioxygenase gene can be detected easily and rapidly by the method of detecting microorganisms according to the present invention. Further, the target microorganisms degrading aromatic compounds can be identified easily, rapidly and accurately by the method of identifying microorganisms according to the present invention without using any conventional biochemical examination.

Further, aromatic-degrading bacteria in soil etc. polluted with crude oil can be specifically detected according to the monitoring method of the present invention. Accordingly, because it is possible to detect accurately how aromatic-degrading bacteria have been multiplied, the multiplication of such aromatic-degrading bacteria can be used as an indication of the progress of degradation of crude oil.

Detection of target microorganisms even in a bacterial habitat containing a large number of microorganisms can be ensured by suitably selecting a probe for use in the method of detecting microorganisms according to the present invention. Accordingly, the present invention can also be utilized in e.g. diagnosis of infections requiring monitoring a varying level of the specific microorganisms.

From the foregoing, the present invention is applied not only to bio-remediation technology but also to development of an environmental sanitation system by means of microorganisms as well as to control of food manufacturing step etc. in food industry.

EXAMPLES

Hereinafter, the present invention is described in more detail by reference to Examples, which however are not intended to limit the scope of the present invention.

Example 1
Determination of preserved amino acid sequences

Amino acid sequences encoded by dioxygenase genes from 11 aromatic-degrading bacteria were retrieved from SWISS PROT and aligned using software of Gene Works to examine the presence of preserved amino acid sequences among them. It was revealed that a plurality of preserved amino acids are present in the amino acid sequence of the large subunit of dioxygenase, and that these amino acids consist of 6 amino acids and 7 amino acids respectively.

Said amino acid sequences were compared, and among them, the amino acid sequences each consisting of 6 amino acids were designated amino acid sequences 1 and 2, and the downstream amino acid sequence consisting of 7 amino acids was designated sequence 3. The results are shown in FIGS. 1 and 2.

By determining and comparing the amino acid sequences as described above, it was revealed that in amino acid sequences 1 and 2, the underlined amino acid sequences at the 1-position and the 4- to 6-positions from the N-terminal of these amino acid sequences are highly preserved regions, and also that in the amino acid sequence 3, the underlined amino acid sequences at the 1- to 3-positions and the 7-position from the C-terminal of this amino acid sequence are highly preserved regions.

The amino acid sequence of the large subunit in 1,2-dioxygenase from *Pseudomonas putida* F1 strain (SWISS PROT) was determined in the above-described manner and compared. It was revealed that this sequence corresponds to amino acids 116 to 121 and amino acids 208 to 214 in the amino acid sequence coded for by the 1,2-dioxygenase gene from the above strain.

Example 2
Design and preparation of primers

Nucleotide sequences corresponding to the amino acid sequences shown in FIGS. 1 and 2 were determined, and on the basis of these sequences, sense and antisense primers consisting of the nucleotide sequences shown respectively in the frames in FIGS. 1 and 2 were designed.

The designed sense primer contains a nucleotide sequence encoding said preserved amino acid sequence, and so does the antisense primer. However, although it is important for the end of the antisense primer to be specific, the third nucleotide in the codon corresponding to glutamic acid at the C-terminal of this primer is unspecific, so the sequence from which the third nucleotide had been deleted was used.

In the manner as described above, 18-mer sense primer (SEQ ID NO.:4) and 20-mer antisense primer (SEQ ID NO.:5) for use in PCR were prepared respectively as a mixture of 128 kinds of primer. These primers are shown in FIG. 3. If one amino acid in the sequences shown in FIGS. 1 and 2 is coded for by two or more codons, said amino acid is given its corresponding codons in a bracket in FIG. 3.

Example 3
Detection and identification of aromatic-degrading bacteria by use of the primers Using the sense (SEQ ID NO.:4) and antisense (SEQ ID NO.:5) primers prepared in Example 2, PCR was conducted where the following DNAs from aromatic-degrading bacteria were used as templates.
(1) Microbial DNAs used as templates:
(a) DNAs from biphenyl-degrading bacteria: Pseudomonas sp. strain ATCC53643, *Pseudomonas pseudoalkaligenes* KF707, and Alcaligenes sp. strain ATCC53640;
(b) DNAs from naphthalene-degrading bacteria: Pseudomonas sp. strain ATCC17483, *Pseudomonas putida* ATCC17484, and *Pseudomonas putida* PpG7;
(c) DNA from a toluene-degrading bacterium: *Pseudomonas putida* mt-2;
(d) DNA from a benzene- and phenanthrene-degrading bacterium: *Pseudomonas putida* PB4;
(e) DNAs from unidentified novel hydrocarbon-degrading bacteria: MBI 1340, MBI 1422, NAD1; and
(f) DNA from a phenanthrene-degrading bacterium: Sphingomonas sp. strain TB4.

Among the above-enumerated bacteria, two strains *Pseudomonas putida* mt-2 and *Pseudomonas putida* PpG7 are strains carrying the 1,2-dioxygenase gene on a plasmid. On the other hand, eleven strains Pseudomonas sp. strain ATCC53643, Pseudomonas sp. strain ATCC17483, *Pseudomonas putida* KT2440, *Pseudomonas putida* ATCC17484, *Pseudomonas pseudoalkaligenes* KF707, Alcaligenes sp. strain ATCC53640, *Pseudomonas putida* PB4, Sphingomonas sp. strain TB4, and the unidentified hydrocarbon-degrading bacteria (MBI 1340, MBI 1422, and NAD1) are strains carrying the dioxygenase gene on their chromosome.
(2) Culture of the bacteria Marine broth (37.4 g Marine broth (Difco), 30.0 g sodium chloride and 1000.0 ml distilled water) was used to culture Sphingomonas sp. strain TB4, *Pseudomonas putida* PB4, and the unidentified hydrocarbon-degrading bacteria (MBI 1340 and MBI 1422).

Tryptic soy broth (30.0 g Tryptic soy broth (Difco) and 1000.0 ml distilled water) was used to culture *Pseudomonas pseudoalkaligenes* KF707, *Pseudomonas putida* PpG7, Pseudomonas sp. strain ATCC53643, Alcaligenes sp. strain ATCC53640, *Pseudomonas putida* mt-2 and *Pseudomonas putida* KT2440.

A nutrient medium (10.0 g meat extract, 10.0 g peptone, 1.0 g sodium chloride and 400.0 ml distilled water) was used to culture Pseudomonas sp. strain ATCC17483 and *Pseudomonas putida* ATCC17484.

Each bacterium was cultured at 28° C. under shaking until the stationary phase.
(3) Isolation of the dioxygenase gene from the bacteria From the above-enumerated bacteria, the dioxygenase gene was isolated in the following procedures.

Each of the bacteria was cultured as described above, and 6 ml of the culture was removed and centrifuged at 6,000 rpm for 10 minutes to remove the supernatant. The pellet was re-suspended in 2 ml TE buffer containing 120 µl of 10% SDS, 24 µl proteinase K (10 mg/ml) and incubated at 37° C. for 1 hour. 400 µl of 5 M sodium chloride was added to and mixed with it. Then, 320 µl CTAB/NaCl solution was added to it and the mixture was incubated at 65° C. for 20 minutes.

Each bacterium was extracted with an equal volume chloroform/isoamyl alcohol and then centrifuged at 7,000 rpm at room temperature for 10 minutes. Thereafter, it was extracted with an equal volume of TE-saturated phenol and then centrifuged at 7,000 rpm at room temperature for 10 minutes. DNA was precipitated with a 0.6-fold volume of isopropanol and washed with 70% ethanol.

The supernatant was removed and the pellet was re-suspended in 4 ml TE buffer. 20 µl of RNase (20 mg/ml) was added to it and the mixture was incubated at 37° C. for 30 minutes. Thereafter, it was extracted with an equal volume of TE-saturated phenol and then centrifuged at 7,000 rpm at room temperature for 10 minutes.

It was extracted with an equal volume chloroform/isoamyl alcohol and then centrifuged at 7,000 rpm at room temperature for 10 minutes. Thereafter, it was extracted with an equal volume of TE-saturated phenol and then centrifuged at 7,000 rpm at room temperature for 10 minutes. DNA was precipitated with a 0.6-fold volume of isopropanol and washed with 70% ethanol.

The supernatant was removed and the pellet was re-suspended in 4 ml TE buffer to give DNA of each the above bacteria.

(4) Isolation of plasmid DNA

A TNS buffer (10 mM Tris-HCl, pH 8.0, 100 mM NaCl and 20% sucrose), a lysis buffer (100 mM Tris-HCl, pH 8.0, 50 mM EDTA, 0.5 M NaCl, and 2% SDS), an RNase buffer (10 mg/ml pancreas RNase A in 0.1 M sodium acetate, pH 4.8, 0.3 mM EDTA, previously heated at 80° C. for 10 minutes), 3 M NaOH, and 2 M Tris-HCl, pH 5.0, were prepared and used for isolating plasmid DNA in the following procedures.

500 ml culture supernatant of each bacterium was removed and centrifuged at 8,000 rpm (Sorval, GSA rotor) at 4° C. for 20 minutes. The pellet was frozen at 20° C. and thawed at room temperature. This pellet was re-suspended in 100 ml TNS buffer, then 40 ml lysozyme (10 mg/ml in TE buffer) and 3 ml RNase buffer were added to it, and the mixture was incubated on ice for 30 minutes. Then, 120 ml lysis buffer was added to it and the mixture was stirred sufficiently and incubated at 25° C. until the solution became transparent. 3 M NaOH was added dropwise it to adjust its pH to 12.1 under gentle stirring, and thereafter, 2 M Tris-HCl, pH 5.0 was added slowly to it to adjust its pH to 8.5. The amount of the solution was measured, then 5.8 g solid NaCl was added every 100 ml solution so that the final salt concentration was adjusted to 1 M, and the mixture was incubated on ice for 1 hour.

The mixture was centrifuged at 8,000 rpm (Sorval, GSA rotor) at 4° C. for 20 minutes, and the volume of the resulting supernatant was measured, and after PEG 6,000 was added at a final concentration of 5% (w/v), the mixture was left at 4° C. overnight.

The resulting precipitate was centrifuged at 10,000 rpm (Sorval, GSA rotor) at 4° C. for 30 minutes, and the supernatant was removed by decanting. The pellet was re-suspended in 10 ml TE buffer, transferred to another test tube, and extracted 3 times with an equal volume of phenol/chloroform. The resulting aqueous layer was extracted 3 times with chloroform/n-amyl alcohol. The resulting aqueous layers were combined, and CsCl and ethidium bromide were added to it and adjusted so as to attain suitable density for the desired plasmid.

The mixture was centrifuged at 50,000 rpm (Sorval, TV-865 rotor) at 20° C. for 15 hours to give supercoiled plasmid DNA from the mixture. The centrifuge tube was exposed with UV rays, and the DNA was removed through a syringe and then subjected to density gradient centrifugation as described above to give purified plasmid DNA. The ethidium bromide was removed by extraction with water-saturated n-butanol and the CsCl was removed by dialysis against 4 L TE buffer for 24 hours.

These microorganisms were detected by amplifying their specific DNA sequences in PCR where the plasmid DNA obtained in the manner as described above was used as a template.

The conditions for PCR are as follows.

(1) Used reagents

25 µl 10×PCR buffer (100 mM Tris-HCl, pH 8.3, 500 mM KCl, 15 mM $MgCl_2$, 0.01% gelatin (w/v));
0.5 µl sense primer (SEQ ID NO.:4) (100 pmol);
0.5 µl antisense primer (SEQ ID NO.:5) (100 pmol);
2.5 µl dTNPs (2 mM);
1 U of Taq polymerase; and
250 ng template DNA.

Sterilized water was added to the above reagents and the total volume of the solution was adjusted to 25 µl, and it was subjected to PCR under the following reaction conditions.

(2) Reaction conditions

Forty-five cycles, each consisting of reaction at 94° C. for 1 minute, 94° C. for 30 seconds, 55° C. for 1 minute and 72° C. for 1 minute, were conducted, followed by 2 cycles each at 72° C. for 2 minutes.

The amplification products obtained by PCR using DNAs from these microorganisms had an almost similar length of about 318 bp. From the foregoing, it became evident that the microorganisms can be detected by use of the preserved amino acid sequences, regardless of whether these microorganisms have the dioxygenase gene on the chromosome or on a plasmid.

For the microorganisms with substrate specificity as described above, glucose-free M9 medium was prepared where only biphenyl and naphthalene were used as the carbon source. By the plate method, the above-described microorganisms were cultured at 28° C. and the ability of these microorganisms to multiply in the presence of biphenyl and naphthalene as the carbon source was examined. Their multiplication after culture was compared with the nucleotide sequence of their amplification product by the identification method of the present invention. The results are shown in Table 1. From these results, it was revealed that their substrate specificity and the length of their gene amplification product agree with each other, indicating that the present method can be used to identify and judge the microorganisms.

TABLE 1

| Substrate | Strain | PCR amplification |
| --- | --- | --- |
| biphenyl | *Pseudomonas putida* ATCC53643 | + |
| biphenyl | *Alcaligenes* sp. strain ATCC53640 | + |
| biphenyl | *Pseudomonas pseudoalkaligenes* KF707 | + |
| toluene | *Pseudomonas putida* mt-2 | + |
| naphthalene, catechol | *Pseudomonas* sp. strain ATCC17483 | + |
| naphthalene, benzene, phenol | *Pseudomonas putida* ATCC17484 | + |
| naphthalene | *Pseudomonas putida* PpG7 | + |
| catechol | *Pseudomonas putida* KT2440 | + |
| phenanthrene | *Sphingomonas* sp. strain TB4 | + |
| benzene, phenanthrene | *Pseudomonas putida* PB4 | + |
| propylbenzene | MBI 1340* | + |
| naphthalene | NAD1* | + |
| benzene | MBI 1422* | + |

*: Unidentified novel hydrocarbon-degrading bacteria.

What is claimed is:

1. A method of detecting the presence of a microorganism having an aromatic ring hydroxylase dioxygenase in a sample, comprising:

contacting the sample with a nucleotide sequence coding for a sequence of conserved amino acids on an aromatic ring hydroxylase dioxygenase gene under conditions sufficient to allow the polynucleotide sequence to hybridize to nucleic acids in the sample; and measuring hybridization of the nucleotide sequence to the nucleic acids in the sample, wherein hybridization is indicative of the presence of a microorganism having an aromatic ring hydroxylase dioxygenase.

2. The method of claim 1, wherein the nucleotide sequence encodes an amino acid sequences selected from the group consisting of Cys-Ser-Tyr-His-Gly-Trp, Cys-Ser-Phe-His-Gly-Trp, and Glu-Ala-Ala-Phe-Lys-Trp-Asn.

3. The method of claim 1, wherein said microorganisms are aromatic-degrading bacteria.

4. A method for detecting the presence of a microorganism having an aromatic ring hydroxylase dioxygenase in a sample, comprising:

contacting the sample with nucleotide primers coding for a sequence of conserved amino acids of an aromatic ring hydroxylase dioxygenase under conditions sufficient to allow the nucleotide primers to hybridize to a gene encoding the hydroxylase dioxygenase in the sample;

amplifying the nucleic acid sequences in the sample; and measuring the presence of an amplified product corresponding to the dioxygenase gene, wherein the presence of the amplified product is indicative of the presence of a microorganism having an aromatic ring hydroxylase dioxygenase.

5. The method of claim 4, wherein the nucleotide primer encodes an amino acid sequences selected from the group consisting of Cys-Ser-Tyr-His-Gly-Trp, Cys-Ser-Phe-His-Gly-Trp, and Glu-Ala-Ala-Phe-Lys-Trp-Asn.

6. The method of claim 4, wherein said microorganisms are aromatic-degrading bacteria.

7. The method of claim 4, wherein the amplification is by Polymerase Chain Reaction (PCR).

8. A method of monitoring biological degradation of crude oil by detecting the presence of a microorganism having an aromatic ring hydroxylase dioxygenase in a sample, comprising:

contacting the sample with nucleotide primers coding for a sequence of conserved amino acids of an aromatic ring hydroxylase dioxygenase under conditions sufficient to allow the nucleotide primers to hybridize to a gene encoding the hydroxylase dioxygenase in the sample;

amplifying the nucleic acid sequences in the sample; and measuring the presence of an amplified product corresponding to the dioxygenase gene, wherein the presence of the amplified product is indicative of the presence of a microorganism having an aromatic ring hydroxylase dioxygenase.

9. The method of claim 8, wherein the nucleotide primer encodes an amino acid sequences selected from the group consisting of Cys-Ser-Tyr-His-Gly-Trp, Cys-Ser-Phe-His-Gly-Trp, and Glu-Ala-Ala-Phe-Lys-Trp-Asn.

10. The method of claim 8, wherein said microorganisms are aromatic-degrading bacteria.

11. The method of claim 8, wherein the amplification is by Polymerase Chain Reaction (PCR).

* * * * *

SEQUENCE LISTING

<160> NUMBER OF SEQ ID NOS: 5

<210> SEQ ID NO 1
<211> LENGTH: 6
<212> TYPE: PRT
<213> ORGANISM: Dioxygenase

<400> SEQUENCE: 1

Cys Ser Tyr His Gly Trp
 1               5

<210> SEQ ID NO 2
<211> LENGTH: 6
<212> TYPE: PRT
<213> ORGANISM: Dioxygenase

<400> SEQUENCE: 2

Cys Ser Phe His Gly Trp
 1               5

<210> SEQ ID NO 3
<211> LENGTH: 7
<212> TYPE: PRT
<213> ORGANISM: Dioxygenase

<400> SEQUENCE: 3

Glu Ala Ala Phe Lys Trp Asn
 1               5

<210> SEQ ID NO 4
<211> LENGTH: 18
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (1)...(18)
<223> OTHER INFORMATION: n = A,T,C or G
      y = T or C
      w = A or T

<400> SEQUENCE: 4
tgyagytwyc ayggntgg                                                18

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (1)...(20)
<223> OTHER INFORMATION: n = A,T,C or G
      r = A or G
      y = T or C

<400> SEQUENCE: 5
tcngcngcra ayttccartt                                              20